United States Patent
Trousset et al.

(10) Patent No.: US 12,419,601 B2
(45) Date of Patent: Sep. 23, 2025

(54) METHODS AND SYSTEM FOR POSITIONING A C-ARM

(71) Applicant: GE Precision Healthcare LLC, Milwaukee, WI (US)

(72) Inventors: Yves Trousset, Palaiseau (FR); Thomas Benseghir, Le Chesnay Rocquencourt (FR); Raphael Doustaly, Rhône (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 538 days.

(21) Appl. No.: 17/645,232

(22) Filed: Dec. 20, 2021

(65) Prior Publication Data

US 2023/0190218 A1   Jun. 22, 2023

(51) Int. Cl.
  A61B 6/00   (2024.01)
  A61B 6/03   (2006.01)
  A61B 6/40   (2024.01)
  A61B 6/50   (2024.01)

(52) U.S. Cl.
  CPC .............. *A61B 6/545* (2013.01); *A61B 6/032* (2013.01); *A61B 6/4085* (2013.01); *A61B 6/4441* (2013.01); *A61B 6/504* (2013.01); *A61B 6/547* (2013.01)

(58) Field of Classification Search
  CPC .... A61B 6/504; A61B 2090/376; A61B 90/37
  See application file for complete search history.

(56) References Cited

U.S. PATENT DOCUMENTS

| | | |
|---|---|---|
| 6,424,731 B1 | 7/2002 | Launay et al. |
| 7,650,179 B2 | 1/2010 | Redel |
| 8,463,014 B2 | 6/2013 | Movassaghi et al. |
| 8,681,935 B2 | 3/2014 | Ruijters et al. |
| 9,886,756 B2 | 2/2018 | Verstraeten |
| 2002/0006185 A1 | 1/2002 | Lienard et al. |
| 2005/0022158 A1 | 1/2005 | Launay et al. |
| 2007/0274450 A1 | 11/2007 | Niessen |
| 2012/0136236 A1 | 5/2012 | Roberts |
| 2012/0250964 A1* | 10/2012 | Pfister ................. A61B 6/4458 382/130 |

FOREIGN PATENT DOCUMENTS

WO   2016108110 A1   7/2016

OTHER PUBLICATIONS

EP application 22211373.0 filed Dec. 5, 2022—extended Search Report issued Feb. 8, 2023; 9 pages.
Dumay, A. et al., "Determination of Optimal Angiographic Viewing Angles: Basic Principles and Evaluation Study," IEEE Transactions on Medical Imaging, vol. 13, No. 1, Mar. 1994, 12 pages.

* cited by examiner

*Primary Examiner* — Dani Fox
(74) *Attorney, Agent, or Firm* — McCoy Russell LLP (57) ABSTRACT

Various methods and systems are provided for medical imaging. In one embodiment, a method for a C-arm imaging system, comprises during an interventional procedure involving a medical device inserted within a segment of interest (SOI), angulating a C-arm of the C-arm imaging device based on a geometry of the SOI and a location of an extremity of the medical device.

20 Claims, 4 Drawing Sheets

METHODS AND SYSTEM FOR POSITIONING A C-ARM

FIELD

Embodiments of the subject matter disclosed herein relate to medical imaging, and more particularly, to positioning of a C-arm of an x-ray fluoroscopic imaging device relative to an interventional tool within a tubular structure.

BACKGROUND

Non-invasive imaging technologies allow images of internal structures or features of a patient or object to be obtained. In particular, such non-invasive imaging technologies rely on various physical principles, such as the differential transmission of x-rays through a target volume or the reflection of acoustic waves, to acquire data and to construct images or otherwise represent the observed internal features of the patient or object.

For example, in fluoroscopy and other x-ray based imaging technologies such as computed tomography (CT), x-ray radiation is directed toward a subject, typically a patient in a medical diagnostic application, a package or baggage in a security screening application, or a fabricated component in an industrial quality control or inspection application. An imaging system may include an x-ray source and a detector secured to opposite ends of a C-arm. A portion of the radiation impacts a detector where the image data is collected and used in an image generation process. In the images produced by such systems, it may be possible to identify and examine the internal structures and organs within a patient's body, an interventional tool inserted within a region of a patient's body, objects within a package or container, or defects (e.g., cracks) within a fabricated component.

BRIEF DESCRIPTION

In one aspect, a method for a C-arm imaging system, comprises: during an interventional procedure involving a medical device inserted within a section of interest (SOI) in a subject, automatically estimating a position of a C-arm of the C-arm imaging device based on each of a geometry of the SOI and a location of the medical device without input from an operator. In this way, the C-arm may be automatically positioned for optimal imaging during an interventional procedure with increased accuracy and decreased operator effort.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Embodiments of the present disclosure will now be described, by way of example, with reference to the FIGS. 1-2, which relate to various embodiments for adjusting a position of a C-arm with respect to an interventional tool inserted within a region of interest of a patient during an invasive interventional procedure. During an interventional imaging procedure, such as a surgical procedure monitored/assisted by fluoroscopic imaging, continuous, real-time x-ray images of the interventional tool and the patient may be displayed, allowing operators to monitor movement of the inserted interventional tool (also termed "medical device" herein), such as a needle, surgical tool, or scope, relative to anatomical features.

The medical device may be inserted within tubular structures such as a vessel or airway segment during an interventional procedure. While a guided workflow may anticipate the positioning of the medical device according to the procedure being performed and inherent insertion characteristics of the medical device, the guided workflow does not anticipate or adapt for deviations of the medical device from the proposed entry point and pathway. Further, the guided workflow does not provide real-time feedback to the operator performing the insertion regarding their actual trajectory within the patient. For example, even with the guided workflow, precise positioning of the medical device may be challenging. Starting from the puncture site on the patient, it may be difficult for the operator to anticipate if an angulation taken by the medical device will reach the target location. Additionally, respiratory motion of the patient may further complicate precise positioning. This may be especially challenging during the insertion of flexible devices that may deform and deflect during the puncture.

Therefore, optimal automatic positioning of the C-arm is desired for navigating the medical device during the procedure. According to embodiments disclosed herein, angulation of the C-arm may be computed based on a geometry of the tubular structures within which the medical device is being navigated and a current location of a distal extremity of the medical device without intervention from the operator. In the optimal position, the detector of the C-arm device may be substantially parallel to the segment of the tubular structure within which the medical device is navigated.

In this way, by automatically adjusting position of the C-arm during an interventional procedure, imaging of the medical device and the tubular structures within which the medical device is being navigated may be improved. By positioning the C-arm parallel to the segment of the tubular structure within which the medical device is navigated, foreshortening may be reduced and an improved understanding of the anatomy of the SOI may be provided for the operator. Further, by automatically adjusting the position of the C-arm, need for intervention from the operator may be reduced. The technical effect of navigating a real-time virtual trajectory of the medical device, the medical device may be accurately placed more easily and more quickly, reducing an amount of time it takes to perform the procedure and reducing its difficulty as well as potential complications. As a result, the operator may be able to perform more procedures in a given day. Further, patient comfort may be increased by decreasing the procedure time. Further still, a radiation dose provided to the patient may be decreased due to the shortened imaging duration.

Figure 1:
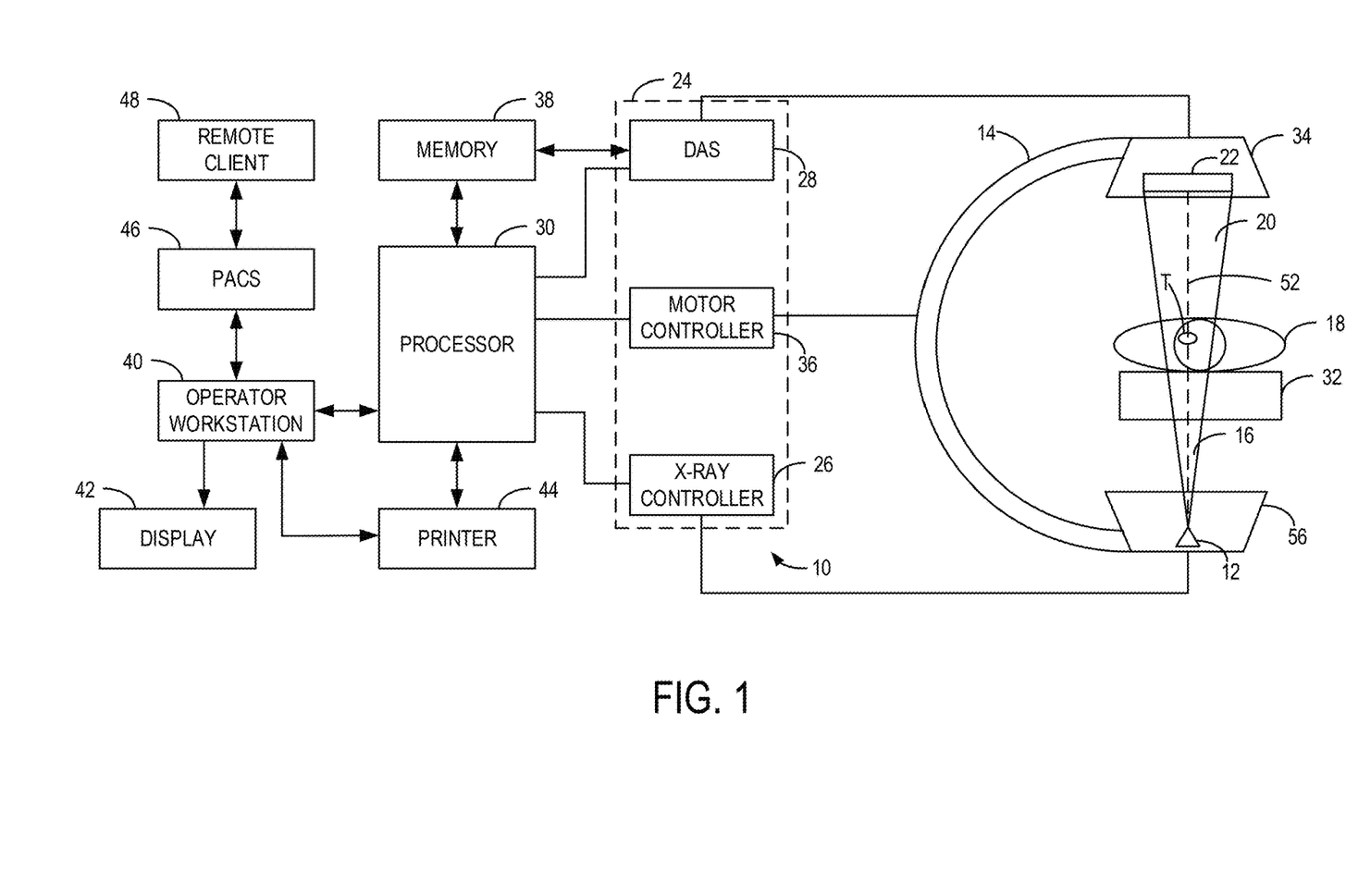
FIG. 1 shows a pictorial view of an imaging system, according to an embodiment.
Figure 3A:
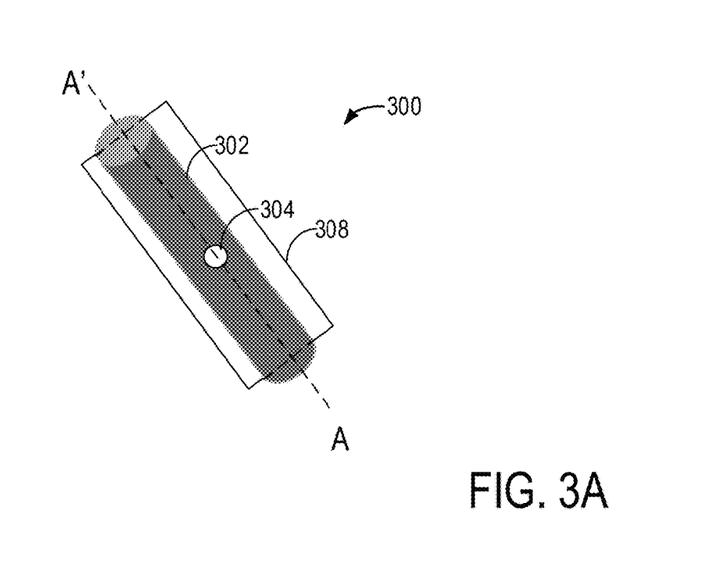
FIG. 3A shows an example schematic of a vessel without bifurcations.
Figure 3B:
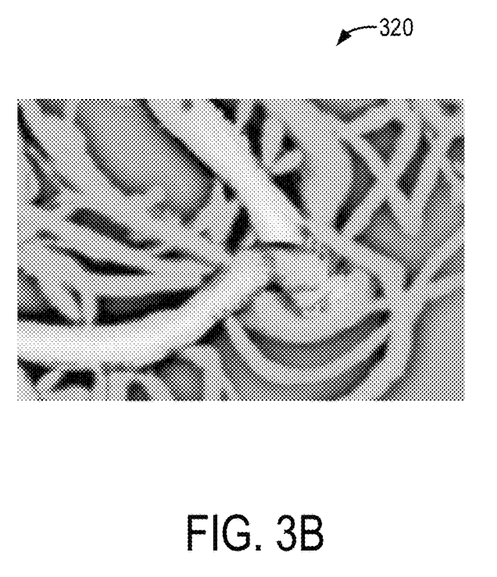
FIG. 3B shows an example image of the vessel as captured by the imaging system prior to adjustment of position of the C-arm.
Figure 4A:
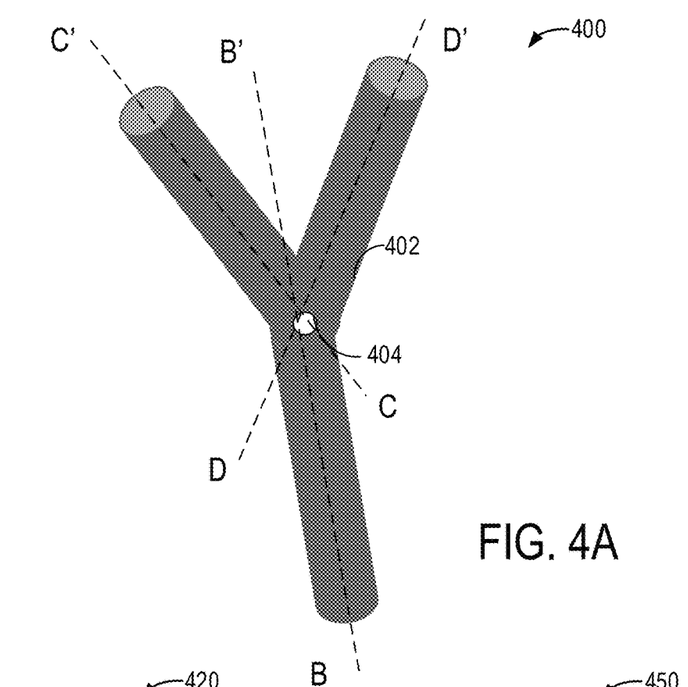
FIG. 4A shows an example schematic of a vessel with bifurcations.
Figure 4B:
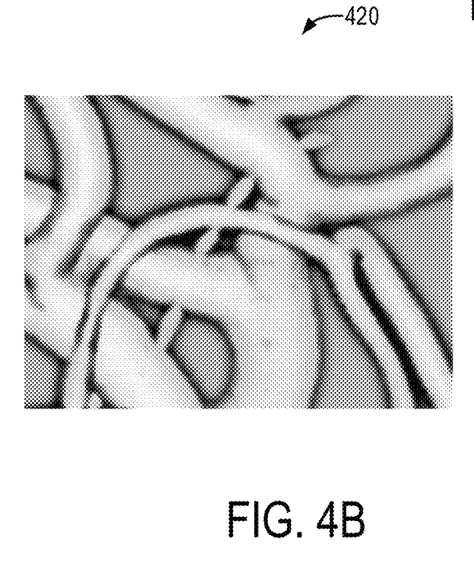
FIG. 4B shows an example image of the vessel with bifurcations as captured by the imaging system prior to adjustment of position of the C-arm.
Figure 4C:
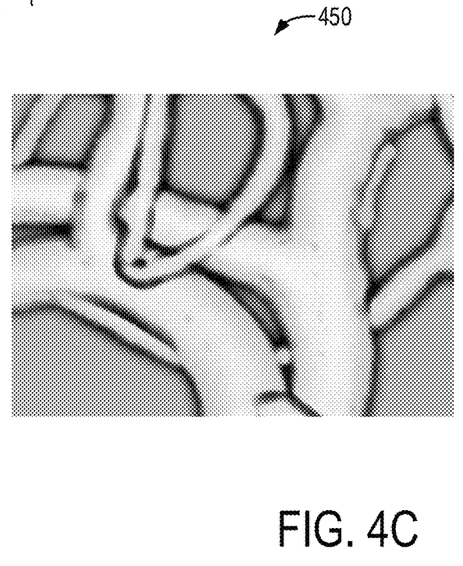
FIG. 4C shows an example image of the vessel with bifurcations as captured by the imaging system after adjustment of position of the C-arm.

An example of a projection imaging system that may be used to acquire medical images of a region of interest is shown in FIG. 1. FIG. 2 provides an example of adjusting a position of a C-arm during an interventional procedure. A tubular structure (vessel) within which a medical device is inserted may be continuous without any bifurcations as shown in FIG. 3A. The segment of interest of the vessel prior to C-arm positioning is shown in FIG. 3B. Upon C-arm positioning, the detector of the C-arm device may be substantially parallel to the segment and the image captured by the imaging device is shown in FIG. 3B. The vessel within which the medical device is inserted may include bifurcations as shown in FIG. 4A. The segment of interest of the bifurcated vessel prior to C-arm positioning is shown in FIG. 4B. Upon C-arm positioning, the detector of the C-arm device may be substantially parallel to a plane of the bifurcation and the image captured by the imaging device is shown in FIG. 4C.

Turning now to the figures, FIG. 1 illustrates diagrammatically an exemplary embodiment of a C-arm imaging system 10 for acquiring and processing image data. In the illustrated embodiment, C-arm imaging system 10 is a digital x-ray system designed both to acquire original image data and to process the image data for display. The C-arm imaging system 10 may be a stationary or mobile x-ray system. In the embodiment illustrated in FIG. 1, the C-arm imaging system 10 is depicted as a C-arm fluoroscopic imaging system, yet it may be understood that other forms of imaging and/or navigation systems may be used within the scope of the present disclosure. For example, it may be understood that the present techniques may also be useful when applied to images acquired using other imaging modalities, such as standard, non-fluoroscopic x-ray imaging, tomosynthesis, and so forth. The present discussion of a fluoroscopic imaging modality is provided merely as an example of one suitable imaging modality. For example, the C-arm imaging system 10 may be any imaging system that acquires two-dimensional images (e.g., slices or projections) of three-dimensional objects.

The C-arm imaging system 10 may acquire x-ray attenuation data at a variety of views around a patient and suitable for tomographic reconstruction. The C-arm imaging system 10 includes an x-ray source 56 secured to a C-arm 14. The x-ray source 56 may exemplarily be an x-ray tube, a distributed x-ray source (such as a solid-state or thermionic x-ray source) or any other source of x-ray radiation suitable for the acquisition of medical or other images. The x-ray source 56 may also be referred to as a radiation source. For example, the x-ray source 56 may comprise an x-ray generator and x-ray tube. The x-ray source 56 emits x-ray radiation 16 from a focal spot 12 in the direction of a subject (or object) 18. For example, the subject 18 may be a patient. In the depicted embodiment, the x-ray radiation 16 is emitted in a cone shape, e.g., a cone-beam. This cone-beam of x-rays pass through an imaged volume of the subject 18. An incident portion (also referred to as incident x-rays) 20 of the x-ray radiation 16 passes through or around the subject 18 and impacts (or impinges on) an x-ray detector 34 including a detector array 22. The x-ray detector 34 may also be referred to as a radiation detector. In the present example, the x-ray detector 34 is a digital x-ray detector and may be portable or permanently mounted to the C-arm imaging system 10. In certain embodiments, the detector array 22 may convert the incident x-ray photons to lower energy photons which are detected. Electrical signals are generated in response to the detected photons, and these signals are processed to reconstruct images of the features (e.g., anatomical features) within the subject 18. Together, the x-ray source 56 and the x-ray detector 34 comprise an x-ray imaging chain.

As an example, the detector array 22 may include one or more complementary metal oxide semiconductor (CMOS) light imager panels, each separately defining an array of detector elements (e.g., pixels). Each detector element produces an electrical signal that represents the intensity of the x-ray beam incident at the position of the detector element when the beam strikes the detector array 22. This signal may be digitized and sent to a monitor/display device for display.

The x-ray source 56 and the x-ray detector 34 are exemplarily controlled by a system controller 24 that provides both power and control signals for the operation of the imaging system 10. The system controller 24 may control the x-ray source 56 via an x-ray controller 26, which may be a component of the system controller 24. In such an embodiment, the x-ray controller 26 may be configured to provide power and timing signals to the x-ray source 56.

The x-ray detector 34 is further exemplarily connected to the system controller 24. The system controller 24 controls the acquisition of the signals generated in the x-ray detector 34 (e.g., by the detector array 22). In an exemplary embodiment, the system controller 24 acquires the signals generated by the detector array 22 using a data acquisition system (DAS) 28. The DAS 28 receives data collected by readout electronics of the x-ray detector 34. The DAS 28 may receive sampled analogue signals from the x-ray detector 34 and convert the data to digital signals for subsequent processing by a processor 30. Alternatively, in other embodiments, the analogue to digital conversion may be performed by circuitry provided on the x-ray detector 34 itself. The system controller 24 may also execute various signal processing and filtration functions with regard to the acquired image signals, such as, but not limited to, initial adjustment of dynamic ranges and interleaving of digital image data.

Further, the x-ray detector 34 includes or communicates with control circuitry in the system controller 24 that commands acquisition of the signals generated in the detector array 22. The x-ray detector 34 may communicate with the system controller 24 via any suitable wireless communication or through a cable or other mechanical connection. Alternatively, operational commands may be implemented within the x-ray detector 34 itself.

The system controller 24 is further operationally connected to the C-arm 14 as well as to a table 32 configured to support the subject 18. A motor controller 36 of the system controller 24 provides instructions and commands to mechanical components of the C-arm 14 and the table 32 to carry out linear and/or rotational movement thereof. The linear and/or rotational movement of the C-arm 14 enables the x-ray source 56 and the x-ray detector 34 to be rotated one or multiple turns about the subject 18, such as rotated primarily in an X-Y plane or angled with respect to the subject. The distance between the x-ray detector 34 and the x-ray source 56 may also be adjusted. Further, the table 32 supporting the subject 18 may be coordinately moved with respect to the movement of the C-arm 14 and/or planned movement of the C-arm 14 to position the patient within the imaging field of view of the imaging system 10. Thus, movement of the patient and/or components of the imaging system to adjust the imaging field of view may include one or both of movements of the C-arm 14 and the table 32.

In general, system controller 24 commands operation of the imaging system 10 (such as via the operation of the x-ray source 56, the x-ray detector 34, and positioning systems described above) to execute examination protocols and to process acquired data. For example, the system controller 24, via the systems and controllers noted above, may rotate a gantry supporting the x-ray source 56 and the x-ray detector 34 about an area of interest or target T so that x-ray attenuation data may be obtained at a variety of views relative to the target T. For example, a central axis 52 of the x-ray radiation 16 may be focused at the target T. In the present example, the system controller 24 may also include signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processor 30 for reconstruction of images. The processor 30 may be one or more conventional microprocessors. The processor 30 configured to execute machine readable instructions stored in non-transitory memory 38. The processor 204 may be single core or multi-core, and the programs executed by the processor 30 may be configured for parallel or distributed processing. In some embodiments, the processor 30 may optionally include individual components that are distributed throughout two or more devices, which may be remotely located and/or configured for coordinated processing. In some embodiments, one or more aspects of the processor 30 may be virtualized and executed by remotely-accessible networked computing devices in a cloud computing configuration. In some embodiments, the processor 30 may include other electronic components capable of carrying out processing functions, such as a digital signal processor, a field-programmable gate array (FPGA), or a graphic board. In some embodiments, the processor 30 may include multiple electronic components capable of carrying out processing functions. For example, the processor 30 may include two or more electronic components selected from a plurality of possible electronic components, including a central processor, a digital signal processor, a field-programmable gate array, and a graphics board. In still further embodiments, the processor 30 may be configured as a graphical processing unit (GPU), including parallel computing architecture and parallel processing capabilities.

The data collected by the DAS 28 may be transmitted to the processor 30 directly or after storage in a memory 38. Any type of memory suitable for storing data might be utilized by the imaging system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction, as described below. One example of image reconstruction may include cone beam computed tomography (CBCT), wherein images acquired at multiple angles about the subject 18 are projected against each other to form voxels of a 3D representation of the imaged region. Other forms of image reconstruction, including but not limited to processing image data from the detector signal to produce clinically useful images, may be used.

The processor 30 may be configured to receive commands and scanning parameters from an operator via an operator workstation 40, typically equipped with a keyboard, touch-screen and/or other input devices. The operator may control the imaging system 10 via the operator workstation 40. Thus, the operator may observe the reconstructed images and/or otherwise operate the imaging system 10 using the operator workstation 40. For example, a display 42 coupled to the operator workstation 40 may be utilized to observe the reconstructed images and to control imaging. Additionally, the images also may be printed by a printer 44 which may be coupled to the operator workstation 40.

Further, the processor 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. The PACS 46 may in turn be coupled to a remote client 48, radiology department information system (RIS), hospital information system (HIS) or to an internal or external network, so that others at different locations may gain access to the raw or processed image data.

While the preceding discussion has described the various exemplary components of the C-arm imaging system 10 separately, these various components may be provided within a common platform or in interconnected platforms. For example, the processor 30, the memory 38, and the operator workstation 40 may be provided collectively as a general or special purpose computer or workstation configured to operate in accordance with the aspects of the present disclosure. In such embodiments, the general or special purpose computer may be provided as a separate component with respect to the data acquisition components of the C-arm imaging system 10 or may be provided in a common platform with such components. Likewise, the system controller 24 may be provided as part of such a computer or workstation or as part of a separate system dedicated to image acquisition.

The C-arm imaging system 10 as shown in FIG. 1 may also include a variety of alternative embodiments generally configured to meet the particular needs of certain applications. For example, the imaging system 10 may be a fixed system, a mobile system, or a mobile C-arm system where the x-ray detector 34 is either permanently mounted inside one end of the C-arm 14 or removable from the system. Further, the imaging system 10 may be a table and/or wall stand system in a fixed x-ray room where the x-ray detector 34 is either permanently mounted together with the system or portable. Alternatively, the imaging system 10 may be a mobile x-ray system with a portable x-ray detector. Such a portable x-ray detector may be further constructed with a detachable tether or cable used to connect the detector readout electronics to the data acquisition system of the scanner. When not in use, the portable x-ray detector may be detached from the scan station for storage or transfer. In practice, the imaging system 10 may be any suitable x-ray based imaging system, including, but not limited to, conventional radiography systems, CT imaging systems, tomosynthesis systems, C-arm systems, fluoroscopy systems, mammography systems, dual- or multiple-energy systems, navigational or interventional imaging systems, and so forth. Further still, while an example of a flat-panel detector was described above, a digital detector system including image intensifier and a video camera may be used to convert the incident x-rays 20 to a video signal.

As used herein, the phrase "reconstructing an image" is not intended to exclude embodiments of the present invention in which data representing an image are generated but a viewable image is not. Therefore, as used herein, the term "image" broadly refers to both viewable images and data representing a viewable image. However, many embodiments generate (or are configured to generate) at least one viewable image.

The subject 18 may be imaged with the x-ray imaging chain, including the x-ray source 56 and the x-ray detector 34. Although not explicitly shown, it may be understood that the x-ray imaging chain may further include various lenses (e.g., a collimating lens and/or a focusing lens) and apertures. The x-ray imaging chain is positioned around the subject 18 at different angles that are chosen by an operator (e.g., a clinician). The subject 18 lays on the table 32, and the position of the table 32 may also change throughout the imaging. The acquired x-ray images are 2D conic projections, and the changes to the imaging chain and the position of the table 32 may enable the operator to see an anatomy of the subject 18 under different angles and magnification factors. For example, a workflow of the imaging procedure may include acquiring several image sequences, which may be used to diagnose and if necessary, intervene on the subject 18. An anatomical place of interest may be viewed in these different images in real-time, which may help guide needle insertions or other interventions.

In this way, the components described in FIG. 1 enable a C-arm imaging system, comprising: a radiation source, coupled at one end of a C-arm, configured to project a beam of radiation toward a subject, a radiation detector, coupled at another, opposite end of the C-arm, configured to receive the beam of radiation projected by the radiation source and impinged by the subject, and a processor operatively coupled to a memory storing instructions that, when executed, cause the processor to: during an interventional procedure, automatically position the radiation detector parallel to a section of interest (SOI) of a subject based on a geometry of the SOI and a location of a medical device inserted within the SOI, without input from an operator. The geometry of the SOI may be based on one or more of cross-sectional images of the SOI obtained via one or more of cone-beam computed tomography systems (CBCT), computerized tomography (CT), and magnetic resonance (MR) prior to the interventional procedure. The location of a medical device within the SOI in three dimensional space is based on one or more x-ray images showing the medical device inserted within the SOI as obtained via the C-arm imaging system.

Figure 2:
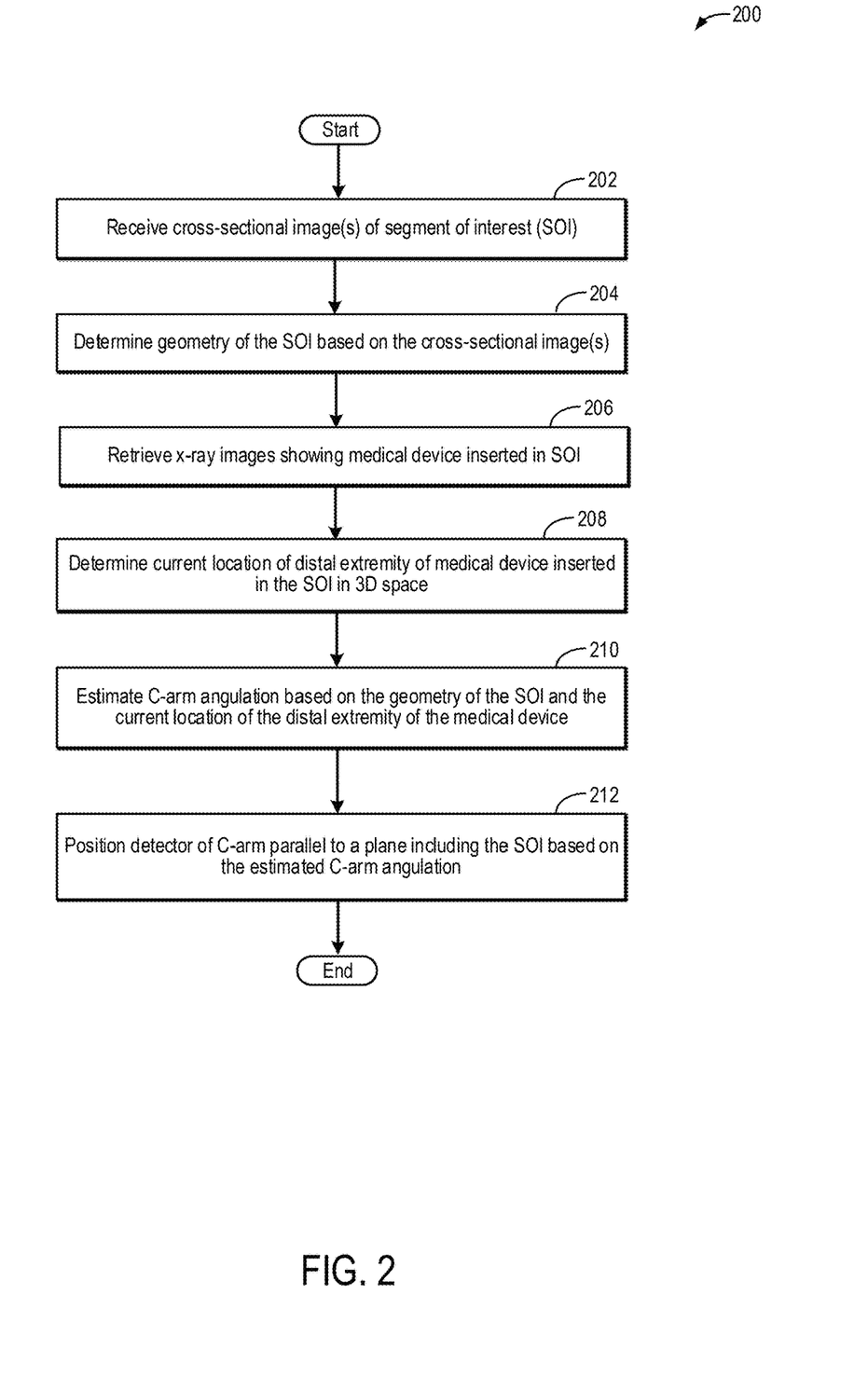
FIG. 2 is a flow chart illustrating a method for adjusting a position of a C-arm during an interventional procedure.

FIG. 2 shows a method 200 for adjusting a position of a C-arm (such as C-arm 14 in FIG. 1) of a C-arm imaging system (such as imaging system 10 in FIG. 1) during an interventional procedure. The method 200 may be carried out during the intervention procedure wherein a medical device is inserted within a segment of interest (SOI) in a patient. As an example, the medical device may be a catheter or a guidewire. The method will be described with regard to the systems and components described herein with respect to FIG. 1, however it may be understood that the method may be implemented with other systems and components without departing from the scope of the present disclosure. The method 200 may be implemented as executable instructions in non-transitory memory of a computing device, such as the memory 38 of FIG. 1, and may be executed by one or more operatively connected processors, such as the processor 30 of FIG. 1, in a coordinated manner. The method 200 will be described with respect to x-ray fluoroscopic imaging, although it may be understood that other imaging modalities may be used without departing from the scope of this disclosure.

At 202, one or more cross-sectional images of the SOI may be retrieved from an external source such as a network drive communicatively connected to the imaging system. The SOI may be a tubular structure such as a vessel or airway segment and the medical device may be inserted within the tubular structure. The medical device may be movable within the segment. In one example, the segment may be a straight or curved tubular structure without bifurcations. In another example, the segment may be a straight or curved tubular structure with bifurcations at which the tubular structure branches out. The SOI may be of a predefined length of the tubular structure within which the medical device is being navigated. The operator may also provide (such as indicate or upload) cross-sectional images of the SOI prior to the imaging. The cross-sectional images may be captured prior to the interventional (operative) procedure using one or more imaging techniques such as cone-beam computed tomography systems (CBCT), computerized tomography (CT), and magnetic resonance (MR).

At 204, the geometry of the SOI may be determined based on the retrieved cross-sectional images. The geometry of the SOI may include a shape and dimensions of the SOI. As an example, for a tubular structure, the radius of the tube, length of the tubes, locations at which the tube branches out, etc. may be determined from the cross-sectional images.

At 206, one or more x-ray images showing the medical device that is inserted within the SOI may be retrieved. The x-ray images may be previously captured by the imaging system or retrieved from an external source such as a network drive communicatively connected to the imaging system. The x-ray images may show the medical device being inserted in the SOI in 2 dimensions. At 208, a current location of a distal extremity of the medical device inserted in the SOI may be determined in 3D space. The current location may be reconstructed from the retrieved one or more x-ray images.

At 210, optimal angulation (position) of the C-arm may be estimated based on the geometry of the SOI and the current location of the distal extremity of the medical device. At the optimal angulation of the C-arm, the image obtained by the C-arm imaging system may facilitate navigation of the medical device within the SOI during interventional cardiology and interventional radiology procedures. At the optimal angulation, the detector coupled to the C-arm is substantially (such as within 5% variation) to parallel to a plane of the SOI. At a bifurcation of the SOI (such as branching in an airway), the detector may be optimally placed substantially parallel to a plane of the bifurcation. The plane of bifurcation may be defined as a plane closest to there or more axes corresponding to each segment of the tubular structure.

At 212, the C-arm may be positioned substantially parallel to a plane including the SOI based on the estimated C-arm angulation. The position of the C-arm may include right anterior oblique (LAO), right atelier oblique (RAO), cranial, and caudal angles. If the optimal position is not attainable in practice due to a possibility of the C-arm coming in contact with another surface (such as a table or the patient) during the movement to that position or at the position, the C-arm may be positioned closest to the estimated C-arm angulation without the possibility of contact. By automatically positioning the C-arm parallel to the plane of the SOI within which the medical device is navigated, need for operator input may be reduced, foreshortening may be reduced, and an improved understanding of the anatomy of the SOI may be provided for the operator. By navigating virtual trajectory of the medical device in real time, the medical device may be accurately monitored, thereby improving accuracy and reducing potential complications.

FIG. 3A shows an example schematic 300 of a segment of interest of a vessel 302 without bifurcations. A medical device 304 may be positioned with the vessel 302 and may move along the length of the vessel such as along the A-A' axis. For optimal imaging, it is desired that the detector of an imaging device including a C-arm to be positioned parallel to a plane of the vessel, such as plane 308. The detector is coupled to one end of the C-arm while the x-ray source is coupled to the other end of the C-arm. The C-arm may be automatically positioned such that the detector is always substantially parallel to the plane of the vessel. In a patient a vessel may be approximated as a tubular curve. A unique plane that best contain the vessel locally may be defined as the plane of the tubular vessel. The plane may be determined with geometric constraints as well as closest angulation.

The position of the C-arm may be automatically estimated device based on each of a geometry of the segment of interest (such as vessel 302) and a location of the medical device without input from an operator. The geometry of the SOI may be estimated from one or more cross-sectional images of the SOI. The cross-sectional images may be retrieved, prior to initiation of the interventional procedure, from an external source including a network drive communicatively connected to the imaging system. The location of an extremity of the medical device may be estimated based on one or more x-ray images showing the medical device inserted within the SOI as obtained by the C-arm imaging system. In response to a path from a current position of the C-arm to the estimated (optimal) position of the C-arm including an obstruction, the C-arm may be moved to a position closest to the estimated position without encountering the obstruction. In the position closest to the prior estimated position, the detector may be substantially parallel to the plane of the SOI.

Figure 3C:
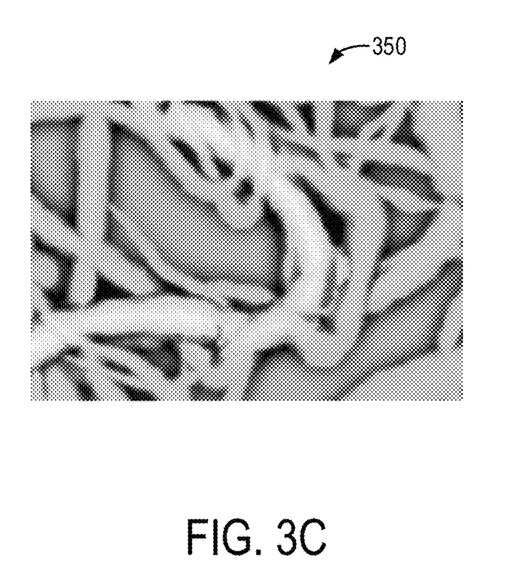
FIG. 3C shows an example image of the vessel as captured by the imaging system after adjustment of position of the C-arm.

FIG. 3B shows an example image 320 of the segment of the vessel 302 as captured by the imaging system prior to adjustment of position of the detector coupled to the C-arm parallel to the plane of the segment. FIG. 3C shows an example image 350 of the segment of the vessel 302 as captured by the imaging system after adjustment of position of the C-arm to position the detector parallel to the plane of the segment. By positioning the detector parallel to the plane of the vessel, an optimal view of the vessel may be obtained which would facilitate navigation of the device 304 within the vessel.

FIG. 4A shows an example schematic 400 of a segment of interest of a vessel 202 with bifurcations. The vessel may include a first, straight section along the axis B-B' which bifurcated into a second section, along the axis C-C' and a third section, along the axis D-D'. A medical device 404 may be positioned with the vessel 402 at the junction of the first, second, and third sections. From the current position of the device 404, the device may move forward to either the second section or the third section. For optimal imaging, it is desired that the detector of an imaging device including a C-arm to be positioned parallel to a plane of the bifurcation. The plane of the bifurcation may be a plane that is closest to including all three axes, B-B', C-C', and D'D' such as having least deviation from each axis. As an example, the plane of the bifurcation may be estimated based on least square regression analysis taking into considering the three axes. The plane of the bifurcation, may pass through each of the first section, the second section, and the third section. The detector is coupled to one end of the C-arm while the x-ray source is coupled to the other end of the C-arm. The C-arm may be automatically positioned such that the detector is always substantially parallel to the plane of the vessel. In this way, for a SOI including a bifurcating tubular structure, the detector may be positioned to be parallel to a plane substantially close to axes of each section of the bifurcating tubular structure.

FIG. 4B shows an example image 420 of the segment of the vessel 402 as captured by the imaging system prior to adjustment of position of the detector coupled to the C-arm parallel to the plane of the segment. FIG. 4C shows an example image 450 of the segment of the vessel 402 as captured by the imaging system after adjustment of position of the C-arm to position the detector parallel to the plane of the segment. By positioning the detector parallel to the plane of the bifurcation vessel, an optimal view of bifurcation of the vessel may be obtained which would facilitate navigation of the device 404 within the vessel to either of the branched sections.

In this way, during an interventional procedure with a medical device inserted within a section of interest (SOI) of a subject, a geometry of the SOI may be estimated, a current location of a distal extremity of the medical device within the SOI may be estimated, a position of a C-arm of the C-arm imaging device may be automatically estimated based on the geometry of the SOI and the current location of the distal extremity of the medical device, and the C-arm may be navigated to the estimated position without input from an operator. By automatically adjusting position of the C-arm during an interventional procedure, without operator input, imaging of the medical device and the tubular structures within which the medical device is being navigated may be improved while saving time and effort from the operator.

An example method for a C-arm imaging system comprises: during an interventional procedure involving a medical device inserted within a section of interest (SOI) in a subject, automatically estimating a position of a C-arm of the C-arm imaging system based on each of a geometry of the SOI and a location of the medical device without input from an operator. In any of the preceding examples, additionally or optionally, the SOI is a tubular structure including one of a vessel and an airway. In any or all of the preceding examples, additionally or optionally, the SOI includes a bifurcating tubular structure with a first segment of the SOI bifurcating into two or more segments. In any or all of the preceding examples, additionally or optionally, the geometry of the SOI is based on one or more cross-sectional images of the SOI. In any or all of the preceding examples, additionally or optionally, the cross-sectional images are retrieved, prior to initiation of the interventional procedure, from an external source including a network drive communicatively connected to the imaging system. In any or all of the preceding examples, additionally or optionally, the one or more cross-sectional images are obtained via one or more of cone-beam computed tomography systems (CBCT), computerized tomography (CT), and magnetic resonance (MR). In any or all of the preceding examples, additionally or optionally, the location of an extremity of the medical device is estimated based on one or more x-ray images showing the medical device inserted within the SOI as obtained by the C-arm imaging system. In any or all of the preceding examples, additionally or optionally, the C-arm imaging system includes an x-ray source coupled to one end of the C-arm and an x-ray detector coupled to another end of the C-arm. Any or all of the preceding examples, the method further comprising, additionally or optionally, moving the C-arm to the estimated position, wherein at the estimated position, the x-ray detector is parallel to a plane of the SOI. In any or all of the preceding examples, additionally or optionally, for a SOI including the bifurcating tubular structure, at the estimated position, the detector is parallel to a plane substantially close to axes of each section of the bifurcating tubular structure. Any or all of the preceding examples, the method further comprising, additionally or optionally, in response to a path from a current position of the C-arm to the estimated position of the C-arm including an obstruction, moving the C-arm to a position closest to the estimated position without encountering the obstruction. In any or all of the preceding examples, additionally or optionally, wherein the medical device is one of a catheter and a guidewire.

Another example method for a C-arm imaging system, comprises: during an interventional procedure with a medical device inserted within a section of interest (SOI) of a subject, estimating a geometry of the SOI, estimating a current location of a distal extremity of the medical device within the SOI, automatically estimating a position of a C-arm of the C-arm imaging system based on the geometry of the SOI and the current location of the distal extremity of the medical device, and navigating the C-arm to the estimated position without input from an operator. In any of the preceding examples, additionally or optionally, the position of the C-arm includes a detector coupled to one end of the C-arm being parallel to a plane including the SOI, the SOI being a tubular structure with or without bifurcations. In any or all of the preceding examples, additionally or optionally, the estimating the geometry of the SOI is based on one or more cross-sectional images of the SOI captured prior to the interventional procedure using one or more imaging techniques including cone-beam computed tomography systems (CBCT), computerized tomography (CT), and magnetic resonance (MR). In any or all of the preceding examples, additionally or optionally, the estimating the current location of the distal extremity of the medical device within the SOI is based on one or more x-ray images showing the medical device inserted within the SOI in two dimensions, the one or more x-ray images being previously captured by the C-arm imaging system or retrieved from an external source communicatively connected to the C-arm imaging system. In any or all of the preceding examples, additionally or optionally, the current location of the distal extremity of the medical device within the SOI is estimated in a three dimensional space based the on one or more x-ray images showing the medical device inserted within the SOI in two dimensions.

Yet another example for C-arm imaging system, comprises: a radiation source, coupled at one end of a C-arm, configured to project a beam of radiation toward a subject, a radiation detector, coupled at another, opposite end of the C-arm, configured to receive the beam of radiation projected by the radiation source and impinged by the subject, and a processor operatively coupled to a memory storing instructions that, when executed, cause the processor to: during an interventional procedure, automatically position the radiation detector parallel to a section of interest (SOI) of the subject based on a geometry of the SOI and a location of a medical device inserted within the SOI, without input from an operator. In any of the preceding examples, additionally or optionally, the geometry of the SOI is based on one or more of cross-sectional images of the SOI obtained via one or more of cone-beam computed tomography systems (CBCT), computerized tomography (CT), and magnetic resonance (MR) prior to the interventional procedure, and wherein the location of a medical device within the SOI in three dimensional space is based on one or more x-ray images showing the medical device inserted within the SOI as obtained via the C-arm imaging system. In any or all of the preceding examples, additionally or optionally, the medical device is one of a catheter, a bronchoscope, and a guidewire, and wherein the SOI is a tubular structure including one of a vessel and an airway.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method for a C-arm imaging system, comprising:
during an interventional procedure involving a medical device inserted within a section of interest (SOI) in a subject, automatically estimating a position of a C-arm of the C-arm imaging system based on each of a geometry of the SOI and a location of the medical device without input from an operator, wherein the location of the medical device includes estimating a current location of the medical device, including a current location of a distal extremity of the medical device in 3D space, and navigating the C-arm to the estimated position, wherein navigating the C-arm to the estimated position includes automatically navigating the C-arm to the estimated position, and wherein estimating the current location of the medical device includes monitoring a virtual trajectory of the medical device in real-time during the interventional procedure.

2. The method of claim 1, wherein the medical device is moved within the SOI, wherein the SOI is a tubular structure including one of a vessel and an airway, and wherein the current location of the medical device is reconstructed from one or more x-ray images showing the medical device being inserted within the SOI as obtained by the C-arm.

3. The method of claim 1, wherein the SOI includes a bifurcating tubular structure with a first tubular segment of the SOI bifurcating into a second tubular segment and a third tubular segment, and wherein the medical device is positioned at a junction of the first tubular segment, the second tubular segment, and third tubular segment.

4. The method of claim 3, wherein for a SOI including the bifurcating tubular structure, at the estimated position, a detector coupled to the C-arm is parallel to a plane of the bifurcating tubular structure substantially close to a first axis of the first tubular segment, a second axis of the second tubular segment, and a third axis of the third tubular segment, and wherein the plane of the bifurcating tubular structure is a plane closest to all three of the first axis, the second axis, and the third axis.

5. The method of claim 4, wherein the plane of the bifurcating tubular structure is estimated based on a least square regression analysis taking into consideration all three of the first axis, the second axis, and the third axis.

6. The method of claim 1, wherein the geometry of the SOI is based on one or more cross-sectional images of the SOI.

7. The method of claim 6, wherein the cross-sectional images are retrieved, prior to initiation of the interventional procedure, from an external source including a network drive communicatively connected to the imaging system.

8. The method of claim 6, wherein the one or more cross-sectional images are obtained via one or more of cone-beam computed tomography systems (CBCT), computerized tomography (CT), and magnetic resonance (MR).

9. The method of claim 1, wherein the C-arm imaging system includes an x-ray source coupled to one end of the C-arm and an x-ray detector coupled to another end of the C-arm.

10. The method of claim 9, wherein at the estimated position, the x-ray detector is substantially parallel to a plane of the SOI.

11. The method of claim 1, further comprising, in response to a path from a current position of the C-arm to the estimated position of the C-arm including an obstruction, moving the C-arm to a position closest to the estimated position without encountering the obstruction.

12. The method of claim 1, further comprising coordinately moving a table supporting the subject with respect to the movement of the C-arm to position the subject within an imaging field of the C-arm imaging system.

13. The method of claim 1, wherein navigating the C-arm to the estimated position includes moving the C-arm linearly and rotationally.

14. A method for a C-arm imaging system, comprising:
during an interventional procedure with a medical device inserted within a section of interest (SOI) of a subject, estimating a geometry of the SOI;
estimating a current location of the medical device, including a current location of a distal extremity of the medical device within the SOI;
automatically estimating a position of a C-arm of the C-arm imaging system based on the geometry of the SOI and the current location of the distal extremity of the medical device in 3D space; and
navigating the C-arm to the estimated position, wherein navigating the C-arm to the estimated position includes automatically navigating the C-arm to the estimated position, and wherein estimating the current location of the medical device includes monitoring a virtual trajectory of the medical device in real-time during the interventional procedure.

15. The method of claim 14, wherein the position of the C-arm includes a detector coupled to one end of the C-arm being parallel to a plane including the SOI, the SOI being a tubular structure with or without bifurcations.

16. The method of claim 14, wherein estimating the geometry of the SOI is based on one or more cross-sectional images of the SOI captured prior to the interventional procedure using one or more imaging techniques including cone-beam computed tomography systems (CBCT), computerized tomography (CT), and magnetic resonance (MR).

17. The method of claim 14, wherein the estimating the current location of the distal extremity of the medical device within the SOI is based on one or more x-ray images showing the medical device inserted within the SOI in two dimensions, the one or more x-ray images being previously captured by the C-arm imaging system or retrieved from an external source communicatively connected to the C-arm imaging system.

18. The method of claim 17, wherein the current location of the distal extremity of the medical device within the SOI is estimated in the 3D space based on one or more x-ray images showing the medical device inserted within the SOI in two dimensions.

19. A C-arm imaging system, comprising:
a radiation source, coupled at one end of a C-arm, configured to project a beam of radiation toward a subject;
a radiation detector, coupled at another, opposite end of the C-arm, configured to receive the beam of radiation projected by the radiation source and impinged by the subject; and
a processor operatively coupled to a memory storing instructions that, when executed, cause the processor to:
during an interventional procedure, estimate a current location of a medical device and automatically navigate the C-arm to an estimated position such that the radiation detector of the C-arm is positioned parallel to a section of interest (SOI) of the subject based on a geometry of the SOI and the current location of the medical device inserted within the SOI, without input from an operator, wherein estimating the current location of the medical device includes estimating a current location of a distal extremity of the medical device in 3D space, wherein estimating the current location of the medical device further includes monitoring a virtual trajectory of the medical device in real-time during the interventional procedure.

20. The system of claim 19, wherein the geometry of the SOI is based on one or more of cross-sectional images of the SOI obtained via one or more of cone-beam computed tomography systems (CBCT), computerized tomography (CT), and magnetic resonance (MR) prior to the interventional procedure, and wherein the location of the medical device within the SOI is based on one or more x-ray images showing the medical device inserted within the SOI as obtained via the C-arm imaging system.

* * * * *